(12) United States Patent
van Asseldonk et al.

(10) Patent No.: US 10,293,130 B2
(45) Date of Patent: May 21, 2019

(54) TRANSTRACHEAL VENTILATION DEVICE

(75) Inventors: Dirk Theodorus Andreas van Asseldonk, Veghel (NL); Mark Hogerwerf, Driebruggen (NL)

(73) Assignee: Ventinova Technologies B.V., Eindhoven (NL)

( * ) Notice: Subject to any disclaimer, the term of this patent is extended or adjusted under 35 U.S.C. 154(b) by 1113 days.

(21) Appl. No.: 14/357,553

(22) PCT Filed: Nov. 11, 2011

(86) PCT No.: PCT/EP2011/069948
§ 371 (c)(1),
(2), (4) Date: Oct. 9, 2014

(87) PCT Pub. No.: WO2013/068047
PCT Pub. Date: May 16, 2013

(65) Prior Publication Data
US 2015/0075535 A1    Mar. 19, 2015

(51) Int. Cl.
*A61M 16/04* (2006.01)
*A61M 16/08* (2006.01)

(52) U.S. Cl.
CPC .... *A61M 16/0497* (2013.01); *A61M 16/0465* (2013.01); *A61M 16/0875* (2013.01)

(58) Field of Classification Search
CPC .............. A61M 16/04; A61M 16/0465; A61M 16/0488; A61M 16/0497; A61M 16/0875
See application file for complete search history.

(56) References Cited

U.S. PATENT DOCUMENTS 3,659,612 A * 5/1972 Shiley ............... A61M 16/0465
                                                                128/207.15
3,987,798 A   10/1976 McGinnis
4,235,229 A   11/1980 Ranford et al.
(Continued)

FOREIGN PATENT DOCUMENTS

DE    10 2009 013205 A1    9/2010
GB         2 137 506 A    10/1984
WO    WO2011038951 A1     4/2011

OTHER PUBLICATIONS

B.S. Vadodaria et al.: "Comparison of four different emergency airway access equipment sets on a human patient simulator", vol. 59, No. 1, Jan. 1, 2004; pp. 73-79, XP55033443; ISSN: 0003-2409; http//dx.doi.org/10.1111/j.1365-2044.2004.03456.x.
(Continued)

*Primary Examiner* — Timothy A Stanis
(74) *Attorney, Agent, or Firm* — Occhiuti & Rohlicek LLP

(57) ABSTRACT

Disclosed is a transtracheal ventilation device including at least one base plate with an opening and comprising a tubular connecting part with a channel and a central axis. The base plate and the connecting part are connected to each other such that a lumen, when inserted into the device, extends into the channel through the opening along the central axis to a fixing element (a fastening). The fixing element can be pivoted relative to the central axis. The fixing element is arranged at a distance of at least 5 millimeters along the central axis from a base plate face which faces away from the fixing element, and the opening has an inner diameter which is at least 20% larger than an outer diameter of the lumen at least on a first plane perpendicular to the central axis.

14 Claims, 3 Drawing Sheets

(56) References Cited

U.S. PATENT DOCUMENTS

Figure 5:
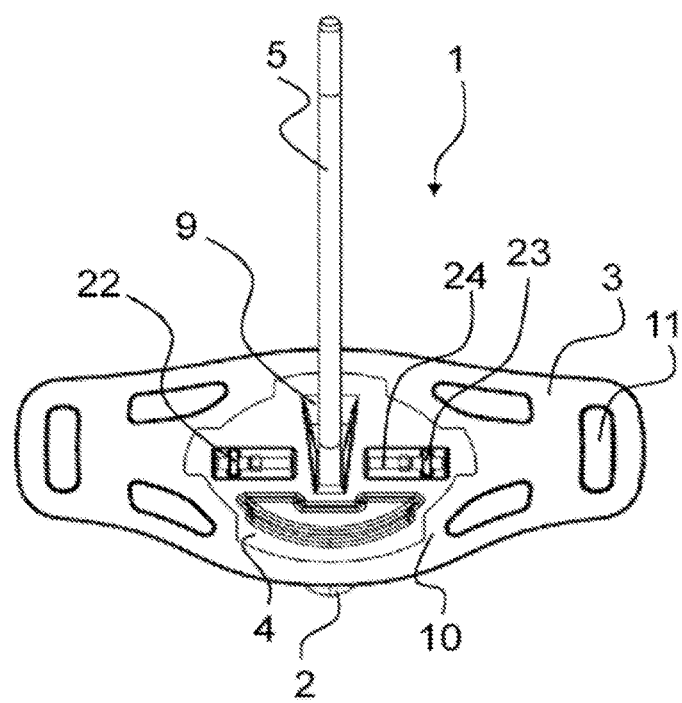

| | | | |
|---|---|---|---|
| 4,817,598 A * | 4/1989 | LaBombard | A61M 16/0465 128/207.14 |
| 4,869,718 A | 9/1989 | Brader | |
| 5,054,482 A * | 10/1991 | Bales | A61M 16/0465 128/207.14 |
| 5,067,496 A * | 11/1991 | Eisele | A61M 16/0465 128/207.14 |
| 5,778,877 A | 7/1998 | Stuart | |
| 5,819,734 A * | 10/1998 | Deily | A61M 16/0465 128/207.15 |
| 6,053,167 A * | 4/2000 | Waldeck | A61M 16/0465 128/200.26 |
| 6,105,577 A * | 8/2000 | Varner | A61M 16/0465 128/207.14 |

OTHER PUBLICATIONS

International Search Report and Written Opinion for PCT/EP2011/069948.

* cited by examiner

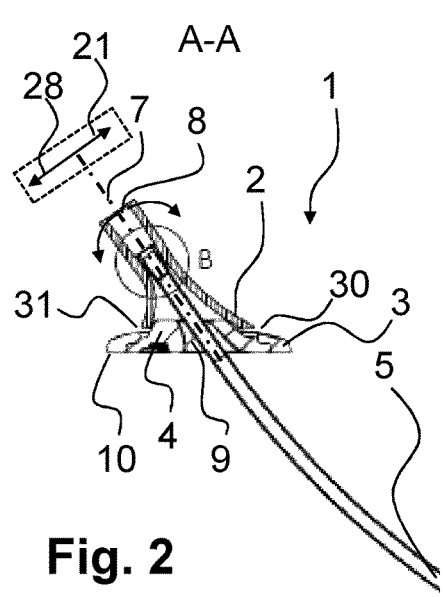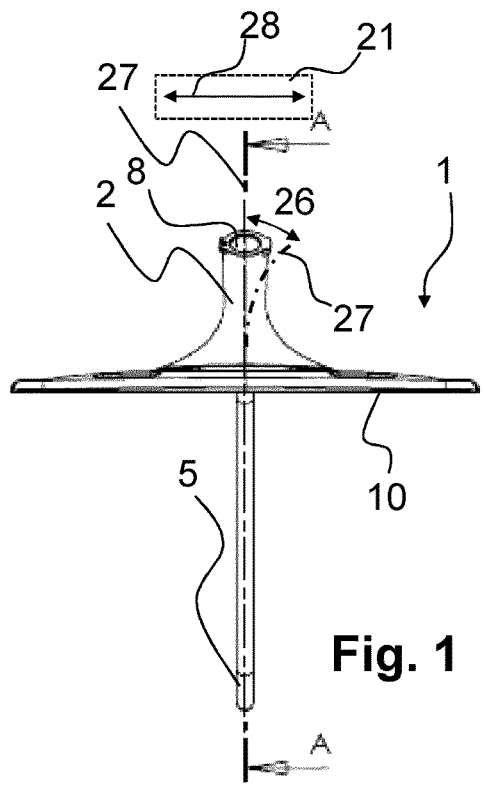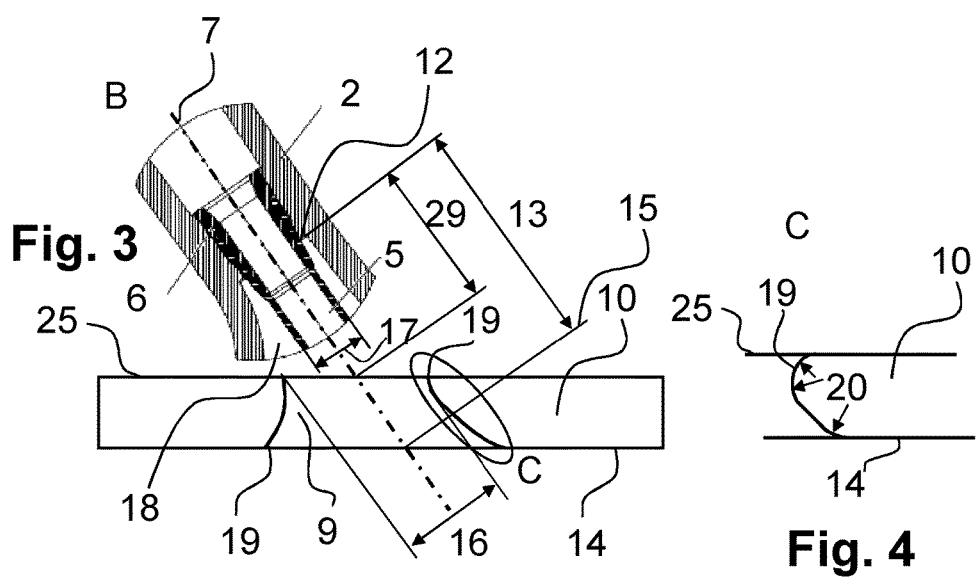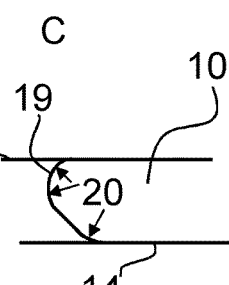

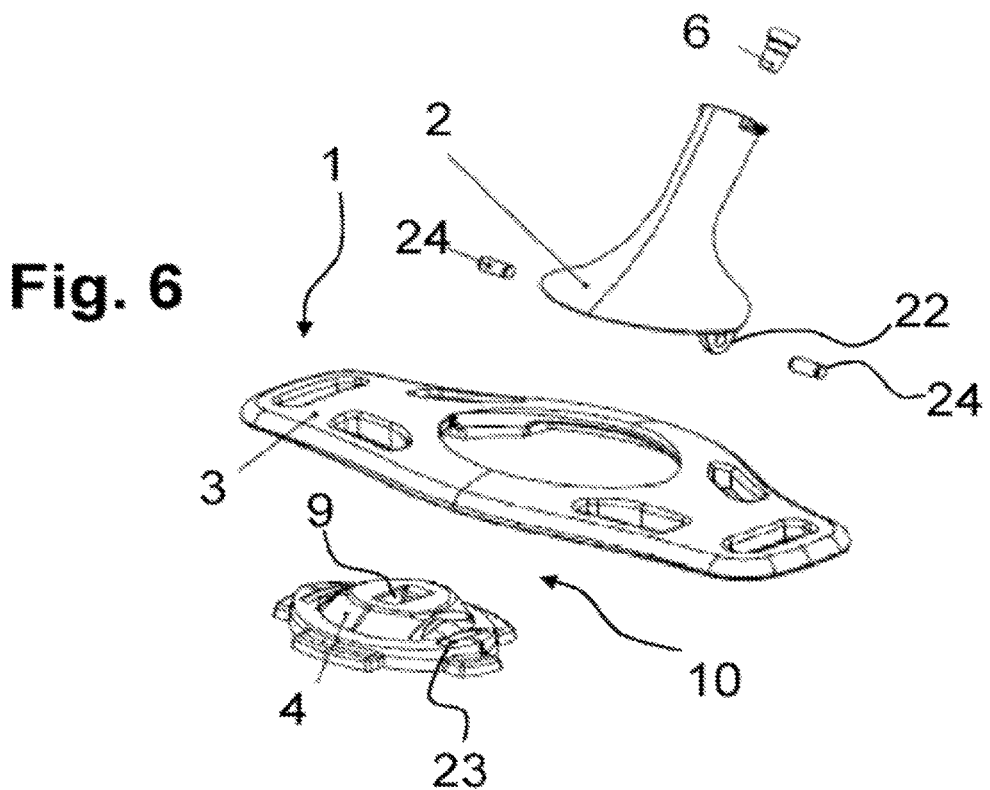

TRANSTRACHEAL VENTILATION DEVICE

The present invention is directed to a device for transtracheal ventilation of human patients. Various devices for transtracheal ventilation are known, e.g. from the article "Comparison of four different emergency airway access equipment sets on a human patient simulator" (Anaesthesia, 2004, 59, pages 73 to 97, FIG. 4). However, the known devices for transtracheal ventilation are suitable only for patients with comparatively normal anatomy.

The present invention now seeks to extend the range of use of transtracheal ventilation and, in particular, to make available to patients with abnormal anatomy, swelling of some kind, bleeding or the like, a device that can be adapted flexibly to such abnormalities. The aim in particular is to ensure that a lumen inserted through the device into the patient is not damaged and/or kinked in the area of the device. Furthermore, the present invention is intended to permit a movement of the patient without the device slipping, or without the patient being caused pain, or even injury, by possible strain on account of the movement of the patient or the movement of the device.

The object of the present invention is therefore to make available a device which allows a patient to breathe by means of transtracheal ventilation, even the patient presents abnormal anatomical conditions, and which prevents damage to a lumen in the area of the device and also compensates for the movements of the patient or of the device.

These objects are achieved by a device as claimed in claim 1. Further advantageous embodiments are set forth in the dependent claims. It should be noted that the features listed individually in the claims can be combined with one another in any technologically appropriate way and form further embodiments of the invention. The description, particularly in connection with the figures, sets forth further illustrative embodiments of the invention.

The device according to the invention for transtracheal ventilation comprises at least a base plate with an opening, and a tubular connecting part with a channel and a geometric central axis. The base plate and the connecting part are connected to each other such that a lumen extends through the opening into the channel along the central axis toward a fastening, by which the lumen can be connected to the connecting part. The fastening is pivotable relative to the central axis. The fastening is arranged at a distance of at least 5 mm [millimeters] along the central axis from a first side of the base plate directed away from the fastening, and the opening, at least in a first plane perpendicular to the central axis, has an internal diameter which is at least 20% greater than an external diameter of the lumen.

DE 10 2009 013 205, the entirety of which is referred to herewith, discloses a catheter for the ventilation of a patient, which catheter here can either be guided through the lumen or replaces the lumen.

In particular, the connecting part is made (at least partially) from a flexible material, such that it is elastically bendable relative to the base plate in relation to the central axis, in particular in all dimensions. In particular, a bend angle of 20°, in particular of 30° and particularly advantageously of 45° is possible in relation to the central axis (and in particular in two directions starting from the central axis), without forces on the base plate having the effect that the patient is inconvenienced by the bending of the connecting part.

In particular, the connecting part is made from a flexurally stiff material and is arranged pivotably on the base plate. In particular, the connecting part is pivotable in at least one second plane, preferably in only one second plane. In particular, a bend angle of 20°, in particular of 30° and particularly advantageously of 45° is possible in relation to the central axis (and in particular in both directions starting from the central axis). The at least one second plane runs in particular in the same plane as the trachea of the patient. The pivoted position of the connecting part (starting from a basic position) is also maintained in particular without the action of an external force.

The pivotable arrangement of the connecting part permits a flexible arrangement of the lumen or of a catheter in relation to the patient. The angle at which the lumen or the catheter is inserted into the patient is now adaptable, by virtue of the pivotable arrangement of the connecting part, to any abnormalities presented by the patient.

In particular, a lumen can be inserted through the open end of the connecting part for guiding a catheter, which can be introduced into the patient. A breathing channel for the delivery and removal of oxygen and/or air extends through the inside of the catheter. The lumen is in particular tubular and flexible. The lumen is inserted into the patient in particular through the trachea of the patient, e.g. via a puncture site on the throat of the patient. The lumen runs along the central axis through the connecting part. On the base plate, the connecting part encloses the opening through which the lumen extends. The lumen can be connected to the connecting part at a fastening, in particular with a force fit and/or form fit. The opening accordingly forms a passage for the lumen/the catheter through the base plate. This passage extends from the second side of the base plate, directed toward the fastening, to the first side of the base plate, directed away from the fastening.

The distance between the fastening and the first side of the base plate directed away from the fastening is determined along the central axis. The fastening ends toward the base plate in particular in a plane perpendicular to the central axis. The intersection of this plane with the central axis defines, together with the intersection between central axis and the plane of the directed away first side of the base plate, the distance between fastening and the directed away first side of the base plate. Thus, the distance can in particular be determined independently of the inclination of the connecting part or of the lumen in relation to the plane formed by the directed away first side of the base plate. In particular, the device lies on the patient via the first side of the base plate directed away from the fastening. The intersection between the central axis and the plane of the directed away first side of the base plate is in particular congruent with the puncture site on the patient, at which site the lumen and/or a catheter enters the patient.

The lumen is in particular inserted into the patient in the area of the intersection between central axis and the plane of the directed away first side of the base plate. The distance of at least 5 mm ensures that the connecting part can be pivoted with the lumen relative to the central axis without causing the patient pain or even injury. Moreover, a kinking of the lumen in the area of the first side of the base plate is avoided. By a corresponding pivoting of the connecting part (and thus of the lumen), it is possible to ensure that the lumen is inserted with the greatest possible bend radius into the patient.

The lumen in the device is connected to the device in particular exclusively via the fastening. The opening in the base plate serves only for the passage of the lumen and provides a free space with respect to the external diameter of the lumen. Thus, the device is able to slip on the neck of the patient without causing the patient pain or even injury on account of a resulting movement of the lumen. The play between opening and lumen also ensures that the lumen is inserted with the greatest possible bend radius into the patient. A kinking of the lumen is avoided. Moreover, the play between opening and lumen and the pivotability of the connecting part ensure that the angle at which the lumen/the catheter is inserted into the patient is adaptable to any abnormalities presented by the patient.

In a first plane perpendicular to the central axis, the opening has an internal diameter which is at least 20% greater than an external diameter of the lumen. The opening is in particular not limited to a circular shape. The term internal diameter refers here only to the smallest dimension of the opening through which the lumen is guided. Accordingly, the lumen too is not limited to a circular shape. The external diameter indicates either the greatest cross-sectional dimension of the lumen or, with a fixed orientation between lumen and opening, the cross-sectional dimension defined respectively for each orientation. Accordingly, the respective associated values for internal diameter of the opening and external diameter of the lumen are to be compared with each other.

The basic position of the central axis is defined by the unloaded arrangement of the device or by a central position. A pivoting of the connecting part or of the fastening relative to the base plate can take place from this basic position.

According to a particularly advantageous embodiment of the device, the distance is at least 8 mm, preferably at least 12 mm, particularly preferably at least 18 mm.

According to another particularly advantageous embodiment, the opening is delimited by at least one edge, wherein the at least one edge has an edge radius of at least 1 mm. An injury or damage to the lumen can be largely avoided by the rounded edges in the area of the opening. Accordingly, preferably all the edges delimiting the opening are to be designed with a corresponding, if appropriate different edge radius. A rounded edge reduces the risk of kinking of the lumen.

In particular, the opening is shaped like a cone, wherein the smaller opening is arranged on the second side of the base plate directed toward the connecting part, and, accordingly, the larger opening is arranged on the first side of the base plate directed away from the connecting part or the fastening. In particular, the opening has a rectangular or elliptical cross section in a plane that runs parallel to the first side of the base plate directed away from the fastening, wherein the greatest dimension of the opening is at least 30% greater than the smallest dimension of the opening.

In particular, the fastening is arranged at a distance of at least 1 millimeter, preferably at least 2.5 millimeters from the second side of the base plate directed toward the fastening. The distance is determined along the central axis. The fastening ends toward the base plate in particular in a plane perpendicular to the central axis. The intersection of this plane with the central axis defines, together with the intersection between central axis and the plane, present in the area of the opening, of the second side of the base plate directed toward the fastening, the distance between fastening and the second side of the base plate directed toward the fastening. Thus, the distance can in particular be determined independently of the inclination of the connecting part or of the lumen in relation to the plane formed by the first side of the base plate.

According to another particularly advantageous embodiment, the fastening is pivotable, in at least one or precisely one second plane parallel to the central axis, through at least 20° [angle degrees], preferably at least 30°, particularly preferably at least 45° to the central axis (and in particular in both directions starting from the central axis). In particular, the fastening is pivotable in all planes which run parallel to the central axis (and through which the central axis extends) through at least 20°, preferably at least 30°, particularly preferably at least 45° to the central axis.

According to another particularly advantageous embodiment of the device, the connecting part is connected releasably to the base plate. A releasable connection means in particular that destruction of (all) the components of the device is not necessary in order to separate the connecting part from the base plate.

The device can thus be used cost-effectively, since cleaning of individual components is possible and, in the event of damage to individual components, the replacement of these individual components is likewise possible.

According to another embodiment, the connecting part is connected non-releasably to the base plate, such that a particularly robust device is created. The connecting part and the base plate can in this case be produced e.g. by two-component injection molding or can be connected to each other by an adhesive.

According to an advantageous development, the connecting part has at least one flange which extends into the base plate, wherein the at least one flange can be connected to the base plate by a form-fit connection.

In particular, the at least one flange is fixed on the base plate by in each case (at least) one fixing element.

The base plate is preferably formed at least by a flange part and a middle part. In particular, the middle part and the connecting part are arranged on mutually opposite sides of the flange part, such that the flange part is held by a releasable connection between the connecting part and the middle part.

In particular, the middle part has a seat and/or a mating piece for the at least one flange of the connecting part, such that the at least one flange can be connected to the middle part. In particular, at least one fixing element is used for fixing the at least one flange on the middle part. This connection is in particular releasable, such that non-destructive separation at least of the components base plate, flange part, middle part and connecting part is possible.

Flange part and middle part are preferably connected to each other non-releasably to form the base plate, such that only non-destructive separation of the components base plate and connecting part is possible. Flange part and middle part can be produced e.g. by two-component injection molding, such that a base plate made from two different materials, each with different material properties, can be produced in one production method. Flange part and middle part are in particular connected non-releasably to each other by an adhesion process and/or a melting process.

In particular, the flange part is designed to be deformable. In this way, the flange part can adapt flexibly to the patient. In particular, the middle part is more flexurally stiff than the flange part or even flexurally stiff. Thus, the connecting part can be attached to the middle part, and a corresponding stiff but pivotable positioning of the connecting part relative to the middle part or relative to the patient is ensured.

According to a preferred embodiment, the connecting part is made (at least partially) from an elastically bendable/deformable material.

According to another preferred embodiment, the connecting part is made from a flexurally stiff material.

In particular, at least a first gap and/or a second gap is provided between connecting part and base plate, which gap permits a pivoting of the connecting part relative to the base plate and substantially limits a bend angle. In particular, upon pivoting of the flexurally stiff connecting part, the first or second gap ensures a bend angle about which the connecting part can be pivoted relative to the base plate from the basic position. The corresponding surfaces of the connecting part and of the base plate delimiting the first and/or second gap form abutments, such that further pivoting is not possible.

According to another embodiment of the device, the open end of the connecting part is designed as a female part of a Luer lock connection. In particular, a positioning aid is provided at the open end, such that a (bent) catheter can be arranged with a predefined orientation in the device.

In particular, the connecting part is provided with two flanges which each extend into in each case at least one corresponding seat of the middle part. In particular, a pin serving as fixing element is inserted through the seat and the respective flanges, such that flanges and middle part are connected to each other with a form fit. In this arrangement, a pivoting about the fixing elements is also possible, such that, in addition to the flexibility of the connecting part, the pivoting of the fastening relative to the base plate is even permitted. It is possible in particular to support this pivoting by making the connecting part from flexible material. However, the connecting part can also be made from a flexurally stiff material that even prevents bending/deformation of the connecting part. In this case, the pivoting of the connecting part is permitted only by the pivotable arrangement of the connecting part on the base plate.

In particular, the at least one flange is formed by a thread, which engages in a mating thread in the middle part. A form-fit connection is thus obtained between the at least one flange and the middle part, or between connecting part and middle part.

It is expressly mentioned that the features directed to the connection of the connecting part to the base plate can also be provided independently of the device according to the invention. In this case, the device for transtracheal ventilation comprises at least a base plate with an opening, and a tubular connecting part with a channel and a central axis. The base plate and the connecting part are connected to each other such that a lumen extends through the opening into the channel along the central axis toward a fastening, by which the lumen can be connected to the connecting part. The connecting part is in particular connected to the base plate releasably and/or with a form fit. In particular, the fastening is pivotable relative to the central axis. The connecting part can be made from flexurally stiff or elastically deformable material.

Further details of the invention and preferred illustrative embodiments are explained below with reference to the figures, without thereby limiting the invention to the illustrative embodiments shown in these. In the schematic drawing:

FIG. 1: shows a device for transtracheal ventilation;
FIG. 2: shows the device according to FIG. 1 in a side view;
FIG. 3: shows a detail from FIG. 2;
FIG. 4: shows a detail from FIG. 3;
FIG. 5: shows a perspective view of the device; and
FIG. 6: shows an exploded view of the device.

FIG. 1 is a schematic view of a device 1 according to the invention for transtracheal ventilation, comprising a base plate 10. The base plate 10 has cutouts for securing fixing straps. These serve to fix the device 1 on a patient. A (flexible) pivotable connecting part 2, arranged on the base plate 10, extends in the direction away from the base plate 10 and from the patient along a central axis 7 and has an open end 8. The connecting part 2 is in particular made from a flexible material, such that it is bendable/pivotable relative to the base plate 10 in relation to the central axis 7, in particular in all dimensions. In particular, a bend angle 26 of 20° [angle degrees], in particular of 30° and particularly advantageously of 45° to the central axis 7 is possible, without forces on the base plate 10 having the effect that the patient is inconvenienced by the pivoting. Through the open end 8 of the connecting part 2, a lumen 5 can be inserted for guiding a catheter that is to be introduced into the patient. A breathing channel for delivery and removal of oxygen and/or air extends through the inside of the catheter. The lumen 5 is tubular and flexible and is inserted through the trachea of the patient, e.g. via a puncture site on the throat of the patient. The lumen 5 is inserted through the open end 8 into the connecting part 2 along the central axis 7. On the base plate 10, the connecting part 2 encloses the opening 9 through which the lumen 5 extends. FIG. 1 also shows the second plane 21 in which the connecting part 2 is pivotable relative to the base plate or to the basic position 27 of the central axis 7. The plane 21 (here indicated by the rectangle shown in broken lines) is spanned by the central axis 7 and the vector 28.

FIG. 2 shows a side view of the device 1 according to FIG. 1 in the section A-A. The base plate 10 is divided into a flange part 3 and a middle part 4, wherein the middle part 4 has an opening 9 for the passage of the lumen 5. The base plate 10 faces with its underside toward the patient, such that the lumen 5 can be inserted through the open end 8 of the connecting part and through the opening 9 into the patient. The connecting part 2 is in particular flexible and, in a second plane 21 (here indicated by the rectangle shown in broken lines), is bendable/pivotable through a bend angle 26 in relation to the basic position 27 of the central axis 7. Here too, the plane 21 is spanned by the central axis 7 and the vector 28. The connecting part 2 is preferably made from a flexurally stiff material such that, in the second plane 21 shown here in FIG. 2, it is pivotable only about a bend angle 26 in relation to the basic position 27 of the central axis 7. Starting from the central axis 7, the bend angle 26 extends in both possible directions in the second plane 21. The second plane 21 in FIG. 2 has another orientation than in FIG. 1. The second plane 21 in FIG. 2 is parallel to the plane in which the trachea of the patient extends.

The connecting part 2 is in particular pivotable in different second planes 21. The lumen 5 extends to near the open end 8 of the connecting part 2 and is there secured in a fastening 12 (see detail B in FIG. 3). However, the lumen 5 can also extend beyond the open end 8 and be connected to the connecting part 2 via the fastening 12. By the division of the base plate 10 into flange part 3 and middle part 4, the base plate 10 can also be made from different materials, e.g. by two-component injection molding, or as individually separate components and can thus be adapted to special requirements.

A first gap 30 and a second gap are provided between connecting part 2 and base plate 10, which gaps permit the pivoting of the (flexurally stiff) connecting part 2 relative to the base plate 10. At the same time, the possible bend angle 26, i.e. the degree of the pivoting in relation to the basic position 27, is defined and limited by the size of the first gap 30 and of the second gap 31.

FIG. 3 shows the detail B according to FIG. 2, wherein the lumen 5 extends into the hollow connecting part 2 and is clamped on a fastening 12 by a sleeve 6, between the wall of the connecting part 2 and the sleeve 6. For this clamping, the connecting part 2 is specifically equipped with a seat, such that secure fixing of the lumen 5 by the fastening 12 is possible and slipping of the lumen 5 in the direction of the base plate 10 or in the direction of the patient is prevented. In particular, the connecting part 2 is designed at the open end 8 as a Luer lock. Here, the connection side provided on the connecting part 2 is designed as a female connection of the Luer lock connection. Along the central axis 7, the channel 18 extends through the connecting part 2 and through the opening 9 in the base plate 10. The lumen 5 now extends into this channel 18, starting from the fastening 12 toward the opening 9. The lumen 5 has an external diameter 17. The opening 9 has an internal diameter 16 in a first plane 15 arranged perpendicular to the central axis 7. This internal diameter 16 is limited by edges 19. Starting from a second side 25 of the base plate 10 oriented toward the fastening 12, the opening 9 widens toward the other, first side 14 of the base plate 10 directed away from the fastening 12. The internal diameter 16 of the opening 9 has a play with respect to the external diameter 17 of the lumen 5, such that, upon pivoting of the connecting part 2 and therefore of the lumen 5, contact between lumen 5 and an edge 19 of the opening 9 is avoided.

The fastening 12 is arranged at a distance 13 from this intersection, or from the first side 14 of the base plate 10 directed away from the fastening. This distance 13 ensures that a pivoting of the fastening 12, i.e. of the lumen 5, in the connecting part 2 is possible, such that as great as possible a bend radius of the lumen 5 is obtained in the area of the device 1. Kinking of the lumen 5, in particular by contact with the edges, is correspondingly prevented. The fastening 12 is arranged at a distance 29 from the second side 25 of the base plate 10 directed toward the fastening 12.

FIG. 4 shows a detail C from FIG. 3. Here, an edge 19 of the opening 9 in the base plate 10 is shown which is defined by an edge radius 20. A sharp edge 19 is thus avoided which could damage the lumen 5 as a result of the latter coming into contact with the edge 19. The opening 9 extends from the second side 25 of the base plate 10 to the first side 14. The individual edges 19 have in particular different edge radii 20.

FIG. 5 is a perspective view showing the underside of the device 1 or of the base plate 10. It shows that the base plate 10 consists of a flange part 3 and of a middle part 4, wherein the middle part 4 has the opening 9 for the lumen 5 to pass through. The flange part 3 has several cutouts 11, wherein the cutouts 11 lying to the outside on the right and left are suitable for securing a neck strap for fixing the device 1 on the patient. The other four cutouts 11, which are arranged in the flange part 3 around the middle part 4, serve for fixing the device 1 on the patient. The opening 9 widening toward the patient is shown in the middle part 4, through which opening the lumen 5 extends starting from the connecting part 2. The connecting part 2 has two flanges 22 (only one being visible here) which extend into the base plate 10 and, via fixing elements 24, form a connection 23 to the middle part 4. A releasable connection 23 is thereby ensured between middle part 4 and connecting part 2. Further clamping elements in particular can be provided which hold the fixing elements 24 permanently in position. These clamping elements can, if appropriate, prevent non-destructive separation of the components flange 22 and middle part.

FIG. 6 shows the device 1 in an exploded view, wherein middle part 4 and flange part 3 are joined together to form the base plate 10. The flexible connecting part 2 is arranged on the base plate 10. The sleeve 6 serves to fix the lumen 5 in the connecting part 2 on the fastening 12. The middle part 4 has an opening 9 that widens toward the patient, and openings for establishing a connection 23 to the flanges 22 of the connecting part 2. For this purpose, fixing elements 24 are provided here as pins, which extend through the flanges 22 and through in each case a corresponding seat in the middle part 4. By means of these fixing elements 24, a connection 23 is established between middle part 4 and connecting part 2, such that the connecting part 2 is fixed (pivotably) on the base plate 10. Only after connecting part 2, flange part 3 and middle part 4 have been brought together are the fixing elements 24 arranged in the middle part in order to produce the connection 23. By the use of the pins as fixing elements 24, an (additional) pivoting movement of the connecting part 2 relative to the base plate 10 is possible, the common axis of the pins in this case forming the pivot axis of the connecting part 2.

LIST OF REFERENCE SIGNS 1 device
2 connecting part
3 flange part
4 middle part
5 lumen
6 sleeve
7 central axis
8 end
9 opening
10 base plate
11 cutout
12 fastening
13 distance
14 first side
15 first plane
16 internal diameter
17 external diameter
18 channel
19 edge
20 edge radius
21 second plane
22 flange
23 connection
24 fixing element
25 second side
26 bend angle
27 basic position
28 vector
29 distance
30 first gap
31 second gap

The invention claimed is:

1. A device for transtracheal ventilation, having at least a base plate with an opening, and a pivotable tubular connecting part with a channel and a central axis, wherein the base plate and the pivotable tubular connecting part are connected to each other such that a lumen inserted into the device extends through the opening into the channel along the central axis toward a pivotable fastening for connection to the pivotable tubular connecting part, wherein the lumen is connected to the pivotable tubular connecting part via the pivotable fastening such that the pivotable fastening and the lumen are pivotable relative to the central axis upon pivoting of the pivotable tubular connecting part with one end of the lumen being configured to be directly inserted through a trachea of a patient via a puncture site on a throat of the patient exposing external surface of the lumen to the trachea, wherein the pivotable fastening is arranged at a distance of at least 5 millimeters along the central axis from a first side of the base plate directed away from the pivotable fastening, and the opening, at least in a first plane perpendicular to the central axis, has an internal diameter which is at least 20% greater than an external diameter of the lumen, wherein the pivotable fastening, in at least a second plane extending parallel to the central axis, is pivotable through at least 20 angle degrees to the central axis, and wherein the pivotable tubular connecting part and the greater diameter of the opening relative to the external diameter of the lumen are configured to define an adaptable angle at which the lumen is inserted into the patient, with the adaptable angle adapted to abnormalities presented by the patient.

2. The device as claimed in claim 1, wherein the distance is within a range of 8 millimeters to 18 millimeters.

3. The device as claimed in claim 1, wherein the opening is delimited by at least one edge, wherein the at least one edge has an edge radius of at least 1 millimeters.

4. The device as claimed in claim 1, wherein the pivotable tubular connecting part is connected releasably to the base plate.

5. The device as claimed in claim 1, wherein the pivotable tubular connecting part has at least one flange which extends into the base plate, wherein the at least one flange is configured to be connected to the base plate by a form-fit connection.

6. The device as claimed in claim 5, wherein the at least one flange is fixed on the base plate by in each case a fixing element.

7. The device as claimed in claim 1, wherein the base plate is formed at least by a flange part and a middle part, wherein the middle part and the pivotable tubular connecting part are arranged on mutually opposite sides of the flange part, such that the flange part is held by a releasable connection between the pivotable tubular connecting part and the middle part.

8. The device as claimed in claim 1, wherein the base plate is formed at least by a flange part and a middle part, wherein the middle part is made from a more flexurally stiff material than the flange part.

9. The device as claimed in claim 1, wherein the base plate is formed at least by a flange part and a middle part, wherein the base plate is produced by a two-component injection-molding method.

10. The device as claimed in claim 1, wherein at least one gap is provided between the pivotable tubular connecting part and the base plate, wherein said at least one gap permits a pivoting of the pivotable tubular connecting part relative to the base plate and substantially limits a bend angle.

11. The device as claimed in claim 1, wherein the pivotable tubular connecting part is made from an elastically bendable material.

12. The device as claimed in claim 1, wherein the pivotable tubular connecting part is made from a flexurally stiff material.

13. The device as claimed in claim 1, wherein upon the pivoting of the pivotable tubular connecting part and resultant pivoting of the pivotable fastening and the lumen, contact between the lumen and an edge of the opening of the base plate, with the opening having the internal diameter which is at least 20% greater than the external diameter of the lumen, is avoided.

14. The device as claimed in claim 1, wherein the opening in the base plate, through which the lumen extends into the channel along the central axis toward the pivotable fastening for connection to the pivotable tubular connecting part, extends from a first side of the base plate, oriented away from the pivotable fastening, to a second side of the base plate oriented toward the pivotable fastening, with the opening widening from the second side of the base plate toward the first side of the base plate.

* * * * *